United States Patent
Pugh et al.

(10) Patent No.: US 8,348,422 B2
(45) Date of Patent: Jan. 8, 2013

(54) APPARATUS AND METHOD FOR ACTIVATION OF COMPONENTS OF AN ENERGIZED OPHTHALMIC LENS

(75) Inventors: Randall B. Pugh, Jacksonville, FL (US); Daniel B. Otts, Jacksonville, FL (US); Frederick A. Flitsch, New Windsor, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/311,652

(22) Filed: Dec. 6, 2011

(65) Prior Publication Data

US 2012/0075574 A1    Mar. 29, 2012

Related U.S. Application Data

(62) Division of application No. 12/577,322, filed on Oct. 12, 2009, now Pat. No. 8,092,013.

(60) Provisional application No. 61/108,957, filed on Oct. 28, 2008.

(51) Int. Cl.
*G02C 7/04* (2006.01)

(52) U.S. Cl. ............... 351/159.02; 351/158; 351/159.03; 632/6.22

(58) Field of Classification Search .................... 351/41, 351/45, 158, 159, 160 R, 161, 163, 168, 177, 351/159.01, 159.02, 159.03, 159.39; 623/6.17, 623/6.19, 6.22
See application file for complete search history.

(56) References Cited

U.S. PATENT DOCUMENTS

| | | | |
|---|---|---|---|
| 4,462,661 A | 7/1984 | Witt | |
| 5,171,266 A * | 12/1992 | Wiley et al. | 623/6.22 |
| 5,233,371 A | 8/1993 | Guillet | |
| 6,096,078 A * | 8/2000 | McDonald | 623/6.22 |
| 6,213,943 B1 | 4/2001 | Abreu | |
| 6,517,203 B1 | 2/2003 | Blum et al. | |
| 8,092,013 B2 * | 1/2012 | Pugh et al. | 351/160 R |
| 2004/0156021 A1 | 8/2004 | Blum et al. | |
| 2005/0036109 A1 | 2/2005 | Blum et al. | |

FOREIGN PATENT DOCUMENTS

| | | |
|---|---|---|
| DE | 19858172 A1 | 6/2000 |
| WO | WO 9203989 A1 | 3/1992 |
| WO | WO 9918879 A1 | 4/1999 |

OTHER PUBLICATIONS

PCT International Search Report, dated Aug. 30, 2010, for PCT Int'l. Appln. No. PCT/US2009/061458.

* cited by examiner

*Primary Examiner* — Huy K Mai
(74) *Attorney, Agent, or Firm* — Joseph P. Kincart

(57) ABSTRACT

This present invention provides apparatus and methods for the activation of an energized ophthalmic lens. In some embodiments, the present invention provides for activation and deactivation of one or more components via wireless communication with an activation unit external to the ophthalmic lens. In some embodiments, an energized ophthalmic lens contains components which detect external signals, process the detected signal and activate components that change optical characteristics via the control of electrical energy.

19 Claims, 5 Drawing Sheets

APPARATUS AND METHOD FOR ACTIVATION OF COMPONENTS OF AN ENERGIZED OPHTHALMIC LENS

CROSS REFERENCE TO RELATED APPLICATIONS

This application is a divisional of U.S. patent application Ser. No. 12/577,322, filed on Oct. 12, 2009, now U.S. Pat. No. 8,092,013, which claims priority to the U.S. Provisional Application No. 61/108,957, filed Oct. 28, 2008, the contents of which are relied upon and incorporated herein.

FIELD OF USE

This invention relates to methods and devices for activating biomedical devices. More specifically, the present invention relates to methods and devices for controlling the application of power to components included in a biomedical device such as an ophthalmic lens.

BACKGROUND OF THE INVENTION

Ophthalmic lenses have successfully functioned for corrective vision purposes for an extensive period. Furthermore, the advancement of the technological field has resulted in numerous complex embodiments that improve the service of needs of ophthalmic patients ranging from permeability of the lens material to designs that accommodate bifocal correction, for example. However, presently available ophthalmic lenses are static.

Numerous functions would be better served if there were the ability to change characteristics of ophthalmic lenses in a controlled manner. At the core of such applications, there remains a need for a means of energizing a function in some manner. In related specifications, which have been incorporated into this specification in their entirety, methods, apparatus and devices which comprise energized ophthalmic lenses have been described. A variety of functions may benefit from energy savings if the energized lens may be activated or deactivated on command. In addition, a benefit may be derived through the application of various states of operation which may be activated by a user. It would therefore, be desirable to incorporate means of activation into energized ophthalmic lenses.

SUMMARY OF THE INVENTION

The present invention is directed to methods and apparatus for activating an energized ophthalmic lens. In general, an energized ophthalmic lens contains a component that has the capability of detecting a signal that is externally generated and to control a function of the lens based upon the detected signal. In some embodiments, the detection of a signal activates a component within the energized ophthalmic lens via the manipulation of electrical power.

Some embodiments of the present invention include one or more detection components operative to detect photon based signals. Detection of photo-based signals may be accomplished, for example, via the use of one or more of: photodiodes, photoresistors, phototransistors and photocells.

Additional embodiments can include an external signal that includes one or more of: electromagnetic energy; inductive coupling; magnetic field coupling; and a signal detected in a capacitive manner. A specific detection device for magnetic field coupling may include, for example, switches with detectors based on the Hall Effect. Various combinations and alternatives of external signal are also within the scope of the invention.

In another aspect, some embodiments of the present invention include methods and apparatus for detection of different types of energy sources. Accordingly, embodiments may include an ophthalmic lens with one or more devices sensitive to one or more of: pressure changes; sound based signals; magnetic forces; light signals; and radio frequency signals.

Some embodiments, additionally relate to methods of providing an external signal and a source of an external signal, which is operative to control power to a component in an ophthalmic lens system, thereby activating or deactivating the component in the ophthalmic lens. Detection of an external signal can cause at least one component included in the ophthalmic lens system to change a physical or electrical state.

In some embodiments the detection can also include processing the signal in an analog or digital manner. Processing may distinguish patterns in the externally generated signals, as for example, two discrete signal events being separated by a band of acceptable time delays. Such a signal combination may be related to physiological characteristics related to blinking of the eyelids.

In some embodiments, an external signal is utilized to electrically activate one or more devices within an ophthalmic lens system and change focal characteristics of an optical device. Still further embodiments may include methods of changing transmittance within electrically active optical devices.

Additionally, an energized ophthalmic lens may have multiple states, such as an active state with normal energy consumptions and a sleep state, including low energy consumption. Activating the lens can cause the circuitry to toggle into and out of a sleep state. During an active state, the lens will become functional and operate at higher energy consumption rates than a sleep state.

In some embodiments the signal detected may also include energy that is useful within the energized ophthalmic lens. Some methods relate to using an external signal to wirelessly provide energy to activate a system that converts the external energy into energy capable of reenergizing the energy source within the energized ophthalmic lens. Some embodiments may relate to the external signal comprising high photon flux which is absorbed and converted into electrical energy for reenergizing the energy source.

Other embodiments relate to the methods that derive from different classes of devices activated by the detection events. Some embodiments of this nature may include identification devices for storing identification information within the lens. Still further embodiments may relate to the method of activating devices capable of displaying information with the energized ophthalmic lens system. Some embodiments may relate to the method of activating devices that cause the excretion of chemicals from within the lens system. In some of these embodiments the chemicals may include pharmaceutical chemicals.

Embodiments may therefore include wireless mechanisms for changing a state of a component or subsystem included in an energized ophthalmic lens via the receipt of a signal. The signal can be verified to ascertain that the signal includes a characteristic used to communicate a command to change a state of a component included within the ophthalmic lens. A change in a state in one or more components in the ophthalmic lens, may thereby be caused based upon the signal.

DETAILED DESCRIPTION OF THE INVENTION

The present invention provides for methods and apparatus for forming an energized ophthalmic lens with one or more components that may be externally activated. In the following sections detailed descriptions of embodiments of the invention will be given. The description of various embodiments are exemplary and the exemplary nature of the embodiments presented do not limit the broadness of the underlying invention.

Glossary

In this description and claims directed to the presented invention, various terms may be used for which the following definitions will apply:

Activate (or Activation): means in an energized ophthalmic lens to enable an energy supply to cause at least a component within the lens to function or change a state of functioning.

Detection: means receiving a signal.

Energized: means the state of being able to provide energy to or have energy stored with, one specific embodiment includes the supply of electrical current to or storage of electrical energy within, an ophthalmic lens.

Energy: means the capacity of a physical system to do work. Many uses within this invention may relate to the said capacity being able to perform electrical actions in doing work.

State: means one of multiple potential defined, discrete physical or electrical conditions, wherein each state may occur within electrical or electro-physical components or system of components included in an energized ophthalmic lens.

Activation Systems within an Activated Energized Ophthalmic Lens

Figure 1:
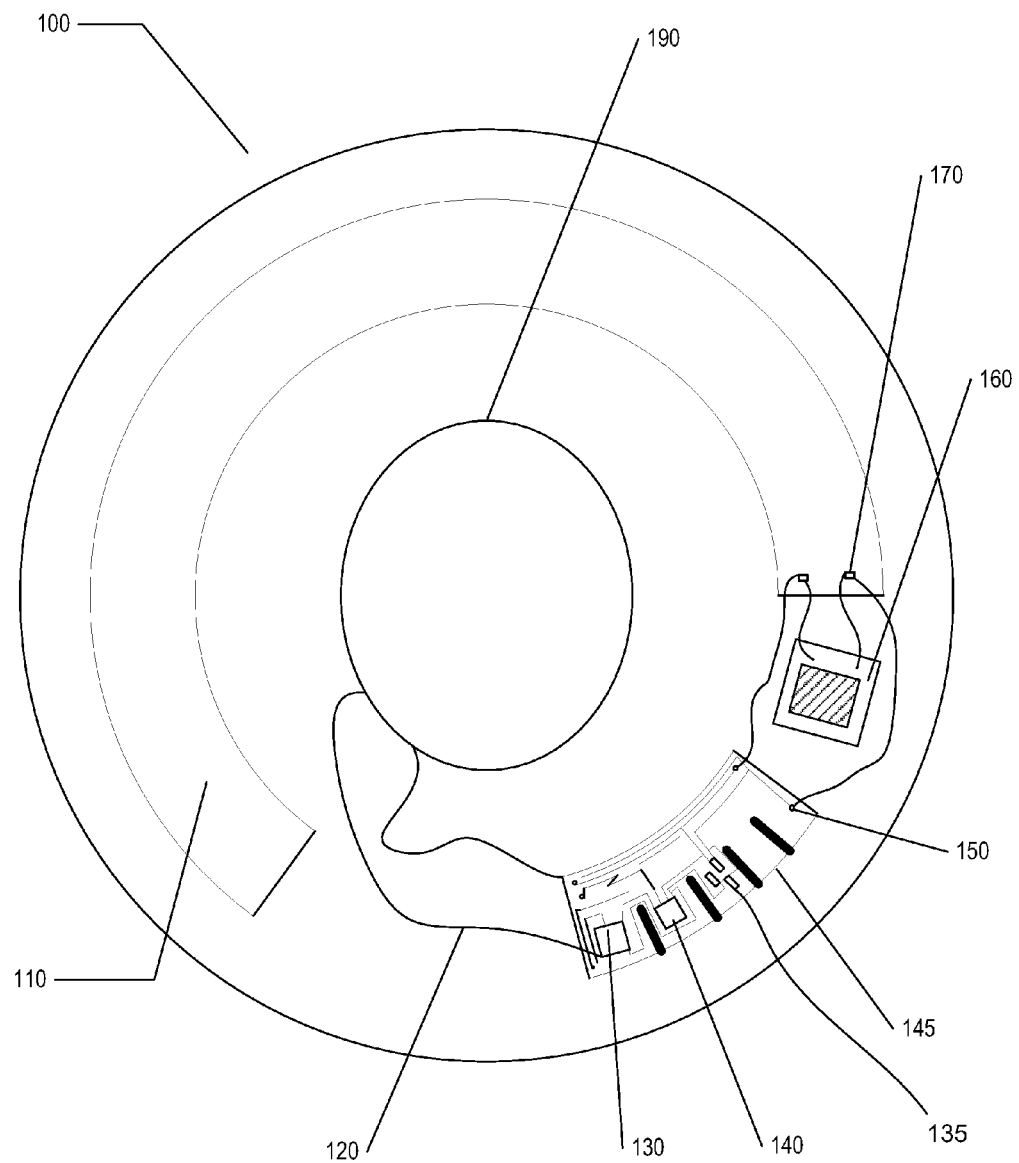
FIG. 1 illustrates an exemplary depiction of an activatable energized ophthalmic lens system.

Referring now to FIG. 1, the basic structure of an exemplary embodiment of an activated and energized ophthalmic lens 100 is illustrated. The energized ophthalmic lens 100 may include one or more components 130, 135, 140 and an energy source 110. In some embodiments, a rechargeable lithium ion battery is included as an energy source 110. The rechargeable battery 110 may be charged through the use of a charging system 160. The charging system 160 can be connected to both the battery energy source 110 and at connection points 170 and to electronic circuit elements 135 at connection points 150. The electronic circuit elements may include one or more of: components 130, 135, 140 mounted to a flexible substrate 145 and shape conforming electronics (not illustrated), such as those including nanonet transistors and carbon nanotube substrates.

Flexible substrates may be useful for the electrical attachment and holding of circuit elements or components 130, 135, 140.

An activation device 140 is useful for changing the state of a controlling device 130. The output of a controller 130 may be routed by wires or other electrical conductors 120 to an electro optic device in the optic zone 190.

Figure 2:
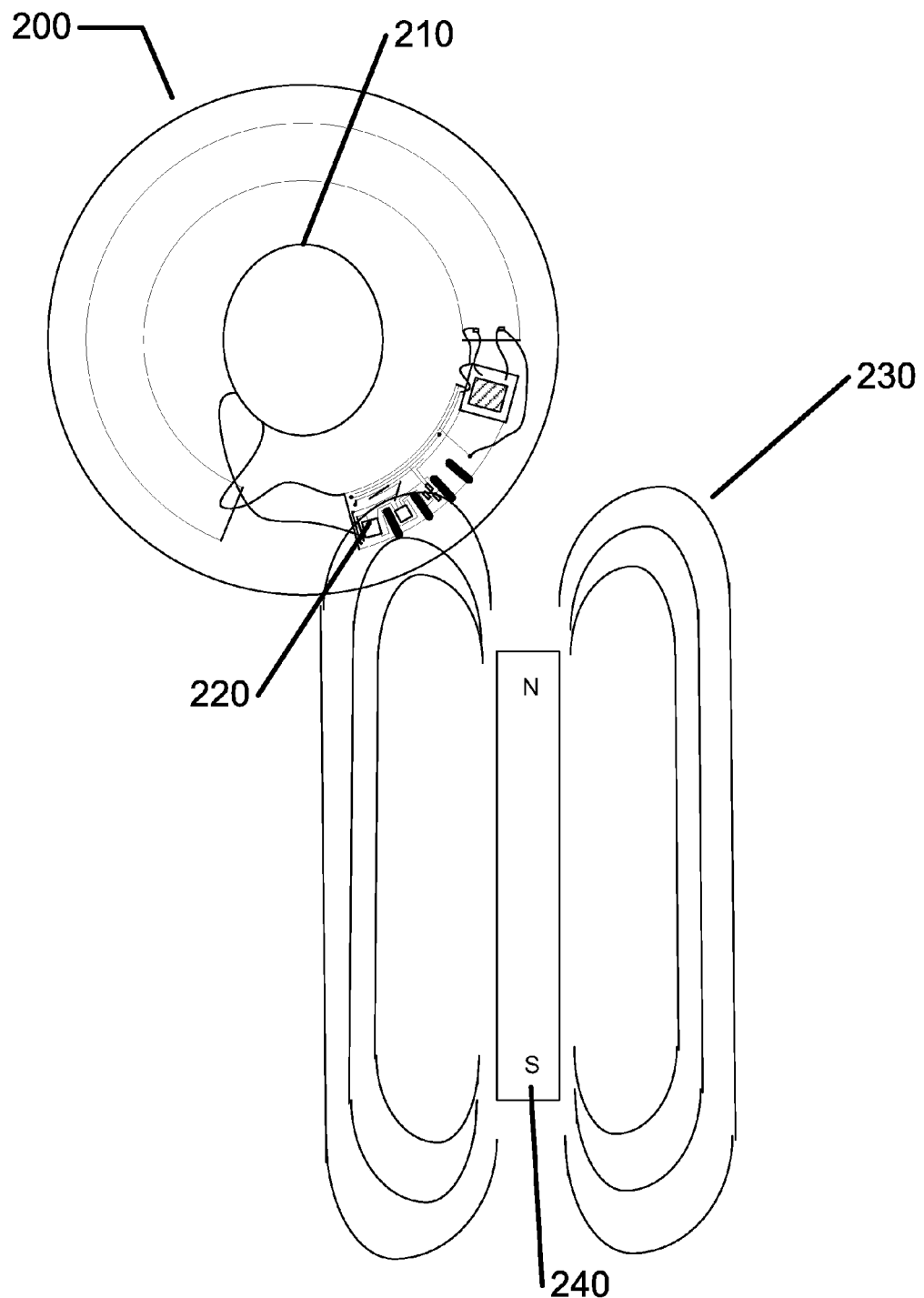
FIG. 2 illustrates an exemplary depiction of an activatable energized ophthalmic lens system activated by the presence of a magnetic signal source.

Proceeding now to FIG. 2, a depiction of some embodiments of the present invention is illustrated with an activation device 220 capable of detecting the presence or absence of a magnetic field of a certain strength. The activation device 220 could monitor for the presence of a change in the magnetic field in its proximate environment. When a magnetic device 240 is brought sufficiently close to the energized ophthalmic lens 200 the device will provide magnetic flux 230 with a density sufficient to trigger a response in the detector 220. The energized lens 200 can be activated based upon the response of the detector 220. Additionally, a state of a component within the lens may be altered based upon the response of the detector 220.

In some embodiments, the change of state of the component may alter a property of an electro-optic device 210 in the optically active portion of the energized ophthalmic lens 200. In a further aspect, in some embodiments, the magnetic activation device 220 may include a Hall Effect sensitive switch. A particular embodiment of such a device may be defined by the use of a micro-sized Hall Effect sensor/switch such as the A1172 manufactured by Allegro Microsystems, Inc. (Worcester, Mass.). It may be apparent to one skilled in the art that there may be numerous sensor devices capable of detecting magnetic fields or changes in magnetic fields and these may define numerous embodiments of an activated ophthalmic lens.

Figure 3:
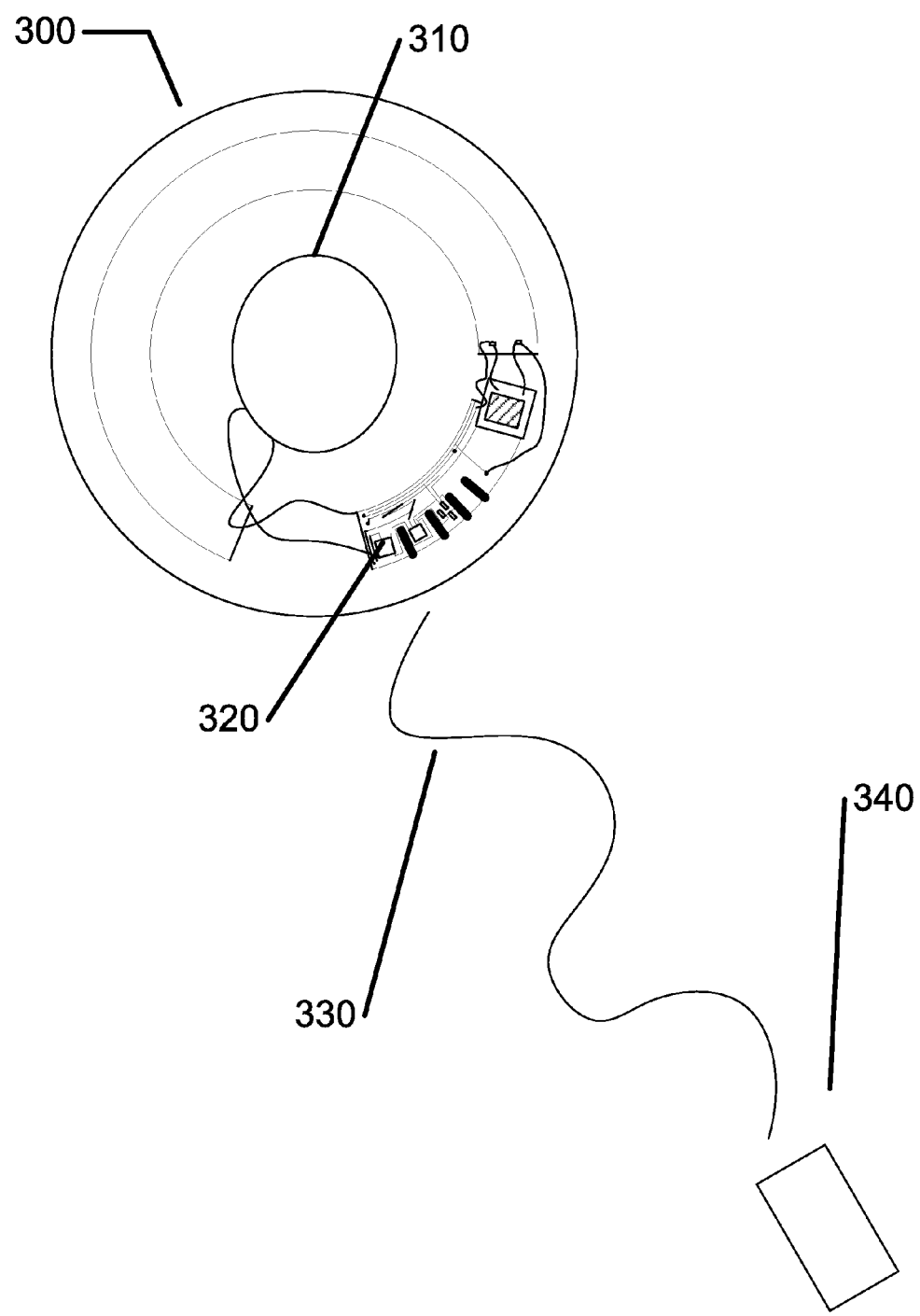
FIG. 3 illustrates an exemplary depiction of an activatable energized ophthalmic lens system activated by an external signal source.

Referring now to FIG. 3, in some additional embodiments, an external signaling device 340 transmits an electromagnetic signal to a receiver device 320 sensitive to the particular electromagnetic signal 330. The receiver device can be used to detect a signal 330 calling for a state change, or in more complicated embodiments a particular electromagnetic signal 330 may comprise a data stream of electromagnetic signals such that when received by device 320 the signal may be converted into activation commands.

In some embodiments, the electromagnetic signal may include a photo source of a particular frequency band. In some of these embodiments, the presence of any signal in the correct frequency band may define an appropriate signal for activation of a component included in an ophthalmic lens.

In different embodiments, the electromagnetic signal, 330, may include photons of a particular energy band where the time evolution of the photon intensity may be absorbed by a detection device 320 and converted into a signal. This signal may then activate various states within the particular ophthalmic lens. Various frequency bands, including visible and infrared may be included as non-limiting examples, and may be used as the electromagnetic signal 330. In other embodiments, the frequency band may comprise radiofrequency based signaling with the numerous embodiment types of signal definitions obvious to one skilled in the art.

In still further embodiments, the source 340 may include a signal whose electric field component contains the signaling information. In some such embodiments, a capacitive coupling device may define the signal detector 320. In analogous manners as discussed for electromagnetic signaling, the presence of such an electric field of a corresponding nature may comprise the signal.

In another aspect, a time evolution of such a signal may encode the appropriate signal being defined for a detection device 320. Other methods and devices utilized in electric field based systems may also be used to activate energized ophthalmic lens components.

Figure 4:
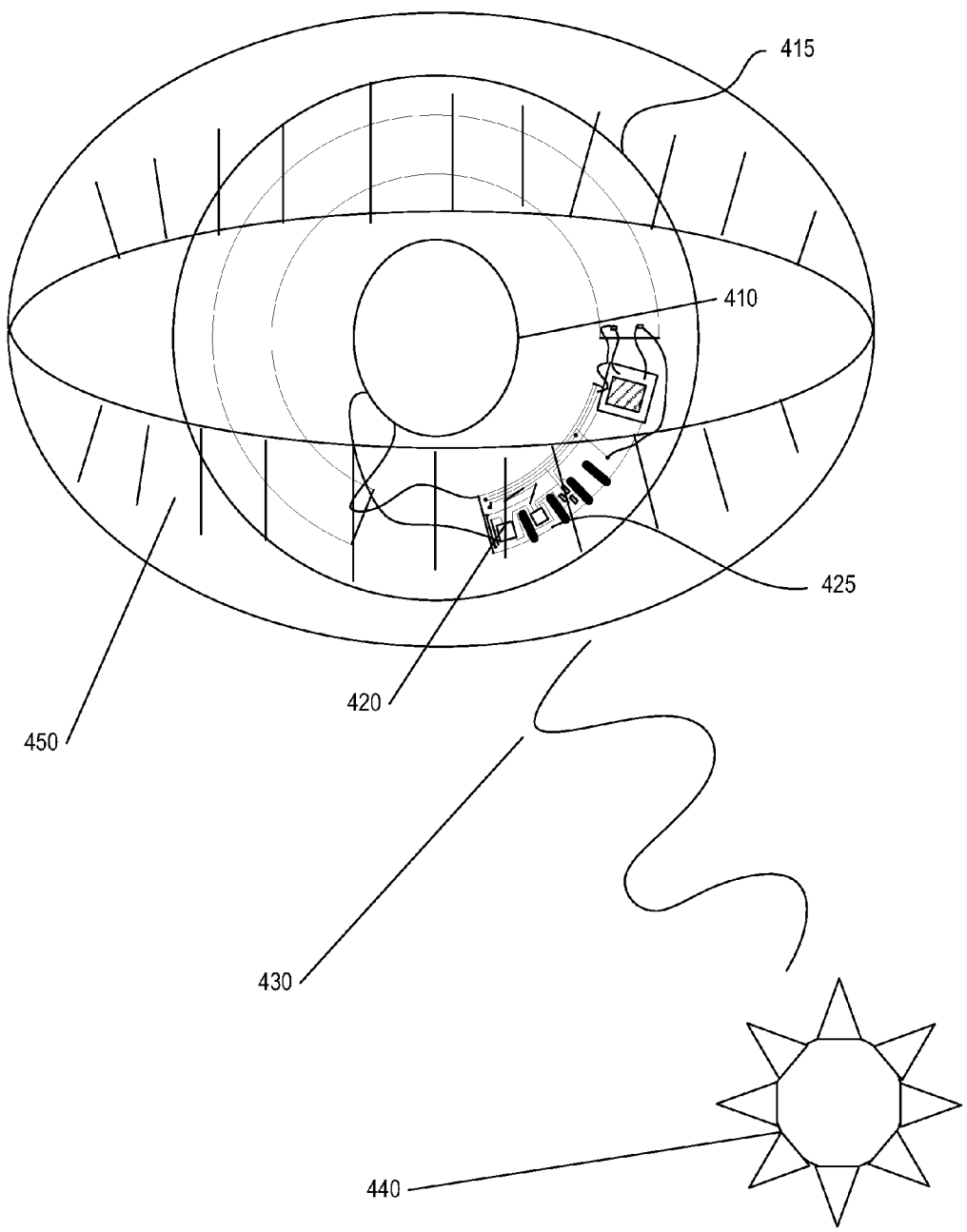
FIG. 4 illustrates an exemplary depiction of an activatable energized ophthalmic lens system in an ambient lighting situation with eyelid blinking signaling.

Referring now to FIG. 4, additional types of activation embodiments are illustrated. An ambient source of light 440, such as, for example, natural sunlight may generate rays of ambient light 430 which impinge in the region around the ophthalmic lens. An ambient source of light 440 may also include artificial light sources such as, for example: incandescent, fluorescent, light emitting diodes or a large variety of ambient light source variations.

A physiological eyelid 450 may represent a relatively opaque screen between the ambient light source 440 and a detector of this light source 420; the presence of light at the detector may define a signaling aspect that may be controlled by the wearer of such an activated energized ophthalmic lens. In an exemplary sense, intentional blinking is used to generate light signal pulses in a light detector 420 included in an energized ophthalmic lens 415 and then used to provide control signals to other components 425 in the energized ophthalmic lens 415. A correct signaling of the light based on eye blinking may therefore activate the lens.

A signal generated by a patterned eye blinking sequence may therefore be utilized to implement a state change of one or more components 425 such as an electro-optic device in the optically active region 410 of the ophthalmic lens system. Multiple alternative embodiments for processing light waves 430 are available from an ambient light source. Variables that may be combined into such embodiments include schemes of signaling via blinking, types of detectors that may detect the light source and electronic components that connect and process signals received and activate components 425 within the energized lens 415.

Figure 5:
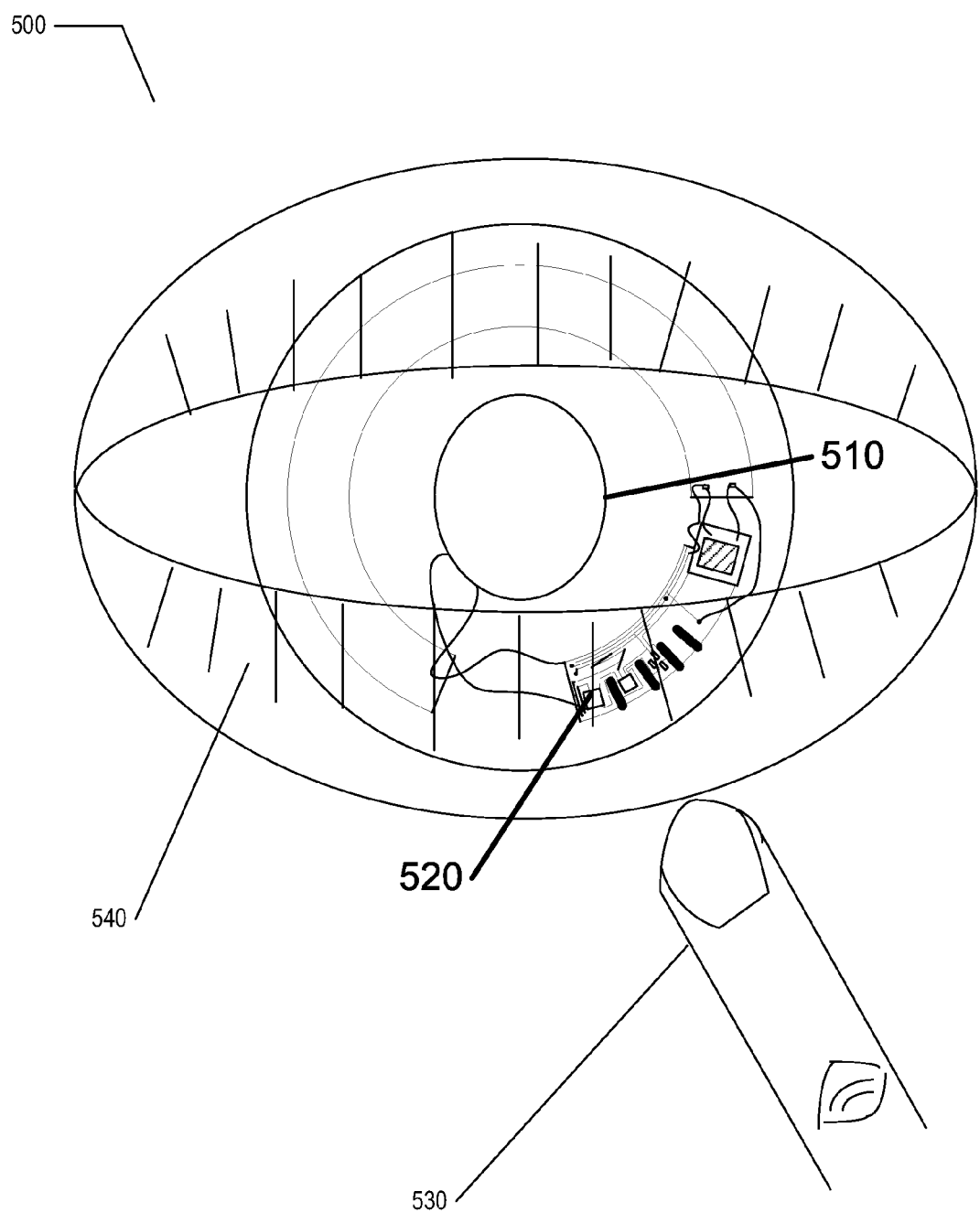
FIG. 5 illustrates an exemplary depiction of an activatable energized ophthalmic lens system activated by an external pressure signal from a fingertip.

Referring now to FIG. 5, in still further embodiments, an activation signal may include mechanical based signaling. Pressure resulting from either mechanical contact or from sound waves may define embodiments where the pressure is analogous to the electromagnetic signals of previous discussion. At 500, an exemplary representation of an ophthalmic region is illustrated where eyelids 540 surround the lens.

In some embodiments, pressure in the form of mechanical contact to the eyelid may be transmitted through the eyelid to a pressure sensitive activation device within the ophthalmic lens. The pressure may be accomplished by pressing a finger against an eyelid. A pressure sensitive device 520 may include a membrane switch; alternatively other pressure sensing devices may also be used, including micro or nano sized pressure transducers. Contact pressure forms a signal; in some embodiments the contact pressure results from a user pressing upon the eyelid with a fingertip 530. Variations relating to the nature of a mechanical or pressure signal and the devices to detect it may comprise art within the scope of this invention.

In alternative embodiments, a pressure signal may be contained in a sound wave. In such embodiments, the structure of this system may be depicted similarly with FIG. 3. In such embodiments, however a source 340 would include one or more sources of sound energy.

Sound energy used to transition the state of an energy receptor may be part of an audible sound regime or alternatively be outside an audible regime. As illustrated, sound waves 330 may be detected by a microphone device 320 or other receptor sensitive to a predetermined wavelength of sound utilized to generate a change of state signal. In such embodiments, a detected sound signal may then trigger activation of components within the ophthalmic lens system. In some embodiments, activation may result in a change in state of an electro-optic device 310. There are numerous variations of this embodiment relating to the nature of the sound wave, its detection, the type of signal contained in the sound wave and the type of activation that it signals.

Function of Activated Energized Ophthalmic Lens Device,

In some embodiments, an energy source within an energized ophthalmic lens may be disconnected from some or all components included in the energized lens, except for relatively small amounts of energy used for circuitry operative to detect activation in one of the manners disclosed. Such an activation signal could then be used to start up one or more additional circuitry sections within the ophthalmic lens. In this manner, activation of the additional circuitry may in its own right activate some function change within the device. Alternatively, in some embodiments, the activation of additional circuitry may allow for the lens to be brought out of what can be called a "sleep mode" and make the lens ready to receive additional activation signals.

In some embodiments the activation signal will change direct aspects of the lens characteristics. For example, the activation signal may change the state of an electroactive lens. In doing so, in some embodiments, the focal characteristics of the ophthalmic lens may be modified. In a non-limiting example, the activation signal may cause electronic circuits to apply a direct current (DC) voltage to electrodes that change the hydrophobicity of an EWOD (Electro Wetting on Dielectric) electrode. Said change in hydrophobicity may alter the characteristics of a meniscus interface and thereby change focal characteristics of a lens formed by this interface. It may be apparent that the same signal may alternatively cause an alternating current (AC) voltage to be applied to the same electrodes. From a more general sense, the activation signal may cause an electroactive lens system to change state from one optical characteristic to another.

In some alternative embodiments, an activation signal may cause changes to the shading of the ophthalmic lens in either optically active or optically non-active regions. Still further activation embodiments may include altering the transmission characteristics of an optically active region of the lens. It may be apparent to one skilled in the art that there are numerous conditions related to how light may be made to proceed through an ophthalmic lens system.

In other embodiments the activation process may comprise signal transmission into the ophthalmic lens. In these cases, the signal may be routed to a processing electronic device within the lens. The signal may comprise a controlling role when decoded within the processing device. Alternatively, the signal may comprise data that is transferred within the lens. This data signal may activate display characteristics within the lens in some embodiments. It may be apparent that various combinations of activation signal may occur within an activated energized ophthalmic lens either in the form of different data encoding of a particular signal type or as a combination of different signal types.

In different types of embodiments, the activation signal may engage transmission of data from the lens itself. In a non-limiting example, an RFID component may be contained within the ophthalmic lens system. Activation may comprise enabling the RFID to transmit a subset of information that it stores. It may be obvious to one skilled in the art that numerous data storage, transmission, processing and communication embodiments may exist within the scope of this art.

In still other embodiments activation of an ophthalmic lens may cause the lens system to dispense one or more of: active agents, chemicals and solutions, from a storage portion in the ophthalmic lens. In some embodiments these active agents, chemicals and solutions may treat an ophthalmic environment into which the lens is placed in some manner. For example, a dispensed solution may include an agent to address dry eye conditions, or a pharmaceutical addressing an eye condition. In some embodiments, a sensor included in the lens may act to monitor a condition in the ophthalmic environment and dispense a solution in response to transitioning into or out of a liminal state. Essentially, the sensor may act as an activation unit. It may be apparent that numerous embodiments of activating the dispensing of chemicals from an activated ophthalmic lens may derive from the art of this invention.

In still other embodiments, the signal may cause the lens system to change physical appearance. By way of non-limiting example a change in physical appearance may involve activation of a light-emitting device. In some embodiments the device may blink on or off while in other embodiments the light may stay in an on state until the reception of another activation signal. It may be apparent to one skilled in the art that there may be numerous embodiments where different types of appearance changes comprise the change in state that is activated within the energized ophthalmic lens.

Conclusion

The present invention, as described above and as further defined by the claims below, provides methods of forming activated energized ophthalmic lenses and apparatus for implementing such methods, as well as descriptions of the activated energized ophthalmic lenses formed thereby and the methods of activation of the lenses.

The invention claimed is:

1. An activation system for an energized ophthalmic lens comprising:
    an energized ophthalmic lens comprising an energy source, wherein the energized ophthalmic lens may be worn such that a physiological eyelid represents one or more of: a screen between an ambient light source and the ophthalmic lens and a mechanical pressure conduit to the ophthalmic lens;
    an activation device in electrical communication with the energy source, wherein the activation device is capable of detecting a signal emanating from a source external to the ophthalmic lens;
    a storage for one or more active agents; and
    a component in electrical communication with the energy source to receive energy from the energy source based upon detection of the external signal by the activation device and cause the ophthalmic lens to excrete one or more of the active agents from the storage portion based upon the detection of the external signal.

2. The activation system of claim 1 wherein the activation device capable of detecting a signal emanating from a source external to the ophthalmic lens comprises a photosensitive device.

3. The activation system of claim 2 wherein the photosensitive device is one or more of: a photodiode, a photoresistor, a phototransistor and a photocell.

4. The activation system of claim 1 wherein the activation device capable of detecting a signal emanating from a source external to the ophthalmic lens comprises a device sensitive to electromagnetic energy in a different spectral region than a photosensitive device.

5. The activation system of claim 1 wherein the activation device capable of detecting a signal emanating from a source external to the ophthalmic lens comprise a device capable of capacitive coupling to an external electric signal.

6. The activation system of claim 1 wherein the activation device capable of detecting a signal emanating from a source external to the ophthalmic lens comprise a device capable of inductive coupling to an external electromagnetic signal.

7. The activation system of claim 1 wherein the activation device capable of detecting a signal emanating from a source external to the ophthalmic lens comprises a device capable of magnetic coupling to an external magnetic signal.

8. The activation system of claim 7 wherein the device capable of magnetic coupling comprises a Hall Effect switch.

9. The activation system of claim 1 wherein the activation device capable of detecting a signal emanating from a source external to the ophthalmic lens comprises a device capable of sensing a change in pressure on a surface of the energized ophthalmic lens.

10. The activation system of claim 1 wherein the activation device capable of detecting a signal emanating from a source external to the ophthalmic lens comprise a device capable of sensing an external sound signal.

11. The activation system of claim 1, wherein the active agent comprises a solution.

12. The activation system of claim 1, wherein the active agent comprises a pharmaceutical.

13. The activation system of claim 1, wherein the active agent is dispensed in response a transition into or out of a luminal state.

14. A method of activating an energized ophthalmic lens comprising:
    providing an external signal source to the energized ophthalmic lens, wherein the energized ophthalmic lens may be worn such that a physiological eyelid represents one or more of: a screen between an ambient light source and the ophthalmic lens and a mechanical pressure conduit to the ophthalmic lens;
    detecting the external signal source via a first component included as a part of the energized ophthalmic lens; and
    altering a state of a second component included as a part of the energized ophthalmic lens, wherein said second component is in electrical communication with an energy source to receive energy from the energy source based upon the detection of the external signal by the first component and cause the ophthalmic lens to excrete one or more of the active agents based upon the detection of the external signal.

15. The method of claim 14 further comprising processing the detection of the external signal to determine an activation state.

16. The method of claim 15 wherein the processing comprises distinguishing two or more discrete detected signals separated by a times delay.

17. The method of claim 16 wherein the timing comprises patterned blinking of eyelids.

18. The method of claim 14 wherein the active agent comprises a chemical in solution.

19. The method of claim 14 wherein the external signal includes data and an active agent dispensed is based upon the data included in the external signal.

* * * * *